United States Patent [19]

Nalewajek et al.

[11] Patent Number: 4,582,652

[45] Date of Patent: Apr. 15, 1986

[54] BASE CATALYZED ISOMERIZATION OF ALLYL PHOSPHONATE DIESTERS TO VINYL PHOSPHONATE DIESTERS

[75] Inventors: David Nalewajek, West Seneca; David S. Soriano, Cheektowaga, both of N.Y.

[73] Assignee: Allied Corporation, Morris Township, Morris County, N.J.

[21] Appl. No.: 627,144

[22] Filed: Jul. 2, 1984

[51] Int. Cl.$^4$ ................................................ C07F 9/40
[52] U.S. Cl. ..................................... 558/88; 558/215; 558/217
[58] Field of Search ................................ 260/989, 956

[56] References Cited

U.S. PATENT DOCUMENTS

| | | | |
|---|---|---|---|
| 631,756 | 8/1899 | Ach | 260/989 |
| 3,597,510 | 8/1971 | Pollak et al. | 260/989 |

*Primary Examiner*—Anton H. Sutto
*Attorney, Agent, or Firm*—Arthur J. Plantamura; Jay P. Friedenson

[57] ABSTRACT

Allyl phosphonate diesters are converted to vinyl phosphonate diesters by isomerization with a catalytically effective amount of one or more metal hydroxide catalysts.

23 Claims, No Drawings

BASE CATALYZED ISOMERIZATION OF ALLYL PHOSPHONATE DIESTERS TO VINYL PHOSPHONATE DIESTERS

BACKGROUND OF THE INVENTION

1. Field of the Invention

This invention relates to an improved process for preparing vinylic pentavalent organophosphorus compounds. More particularly, this invention relates to a process of preparing vinylic pentavalent organophosphorus diester compounds from the corresponding allylic pentavalent organophosphorus diester compound by alkali metal hydroxide induced isomerization.

2. Prior Art

Esters of vinyl phosphonic acid serve as useful reactants in a large number of reactions to form compounds which are useful in agriculture. The versatility of this intermediate material results from reactivity of the vinylic group toward nucleophilic compounds. By manipulations of this reactivity via reaction with nucleophilic compounds such as alcohols, thiols, amines, nitroalkanes, active methylene compounds and the like, a wide class of agricultural chemicals can be prepared. For example, esters of vinylphosphonic acid compounds can be reacted with phosgene or oxalyl chloride to prepare plant growth regulants as described in detail in German Offen No. 2,153,149 (1973). Similarly, such esters can be reacted with amines to accordance with the procedures described in Bartlett et al., Tet letters, 24:2937 (1983) to prepare phosphatase inhibitors.

Furthermore, esters of vinyl-phosphonic acid can be used as precursors in the preparation of compounds which can be used in fields other than agriculture. For example, these compounds can be used in the preparation of heat and light stabilizers for polymers as well as flame retardant or shrinkage retardant additives for polymers. Such uses are described in detail in U.S. Pat. Nos. 4,129,710, 2,784,206 and 2,784,169; Ger. Offen 2,745,982; J. Appl. Polym. Sci. 22:2403–14 (1978); J. Org. Chem (USSR) 19:1789 (1983) and the like.

Heretofore some synthetic procedures for the preparation of vinylic phosphonate compounds have centered on reacting an appropriate vinylic halide with an appropriate trivalent phosphorous esters in accordance with the following reaction scheme:

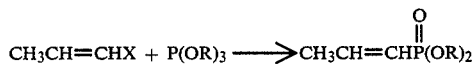

This procedure is known as the Michaeles-Arbuzov reaction. Examples of this procedure are described in "Organic Phosphorous Compounds", Vol. 7 pgs. 1–486, John Wiley & Sons (1976). The Michaeles-Arbuzov reaction suffers from a number of well-known inherent defects. For example, except for the $\alpha,\beta$-unsaturated systems, reactions involving the Michaeles-Arbuzov reaction have failed.

Similarly reactions involving the use of transition metal salt catalyst have been used to prepare vinylic phosphonate compounds. For example, the transition metal salt catalyzed reaction of aromatic and vinylic halides with phosphites or similar trivalent phosphorus compounds to prepare the corresponding vinylic phosphonate compound is described in U.S. Pat. No. 3,493,639. This procedure also suffers from a number of inherent defects. For example, severe reaction conditions have limited the application of this procedure in industrial applications.

It is thus apparent that a need exists for an improved, practical and efficient method for the preparation of vinyl phosphonate esters.

SUMMARY OF THE INVENTION

In accordance with this invention there is provided a novel method of the preparation of vinylic phosphonate compounds. More particularly, this invention provides a method for preparation of a vinylic phosphonate diester compounds of the formula:

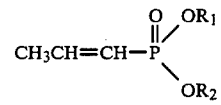

by catalytically isomerizing a compound of the formula:

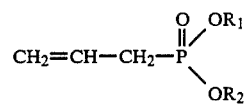

in the presence of a "catalytically effective amount" of one or more a metal hydroxide compounds wherein:

$R_1$ and $R_2$ are the same or different and are alkyl, cycloalkyl, aralkyl, aryl or alkaryl, either unsubstituted or substituted with one or more substituents which are inert under the reaction conditions.

The method of this invention obviates many of the disadvantages associated with the Michaeles-Arbuzov reaction, and affords a simple and non-expensive method for obtaining vinyl phosphonate diesters from readily available precursors in high yields, using short reaction times, and using less stringent reaction conditions.

DESCRIPTION OF THE PREFERRED EMBODIMENTS

This invention relates to a process for preparing vinylic phosphonate compounds. The following compounds can be prepared in accordance with the process of this invention by selecting appropriate starting materials and reaction conditions:

1-methyl,2-vinyl,O,O-dimethyl phosphonate
1-methyl,2-vinyl,O,O-diethyl phosphonate
1 methyl,2,-vinyl,O,O-dipropyl phosphonate
1 methyl,2-vinyl,O,O-diisopropyl phosphonate
1 methyl,2-vinyl,O,O-dibutyl phosphonate
1 methyl,2-vinyl,O,O-di-(butyl)phosphonate
1 methyl,2-vinyl,O,O-di-(2,4,5-trichlorophenyl)phosphonate
1-propenyl,2,5 dioxyphospholidine oxide.

The process of this invention can be conveniently described by the following reaction scheme:

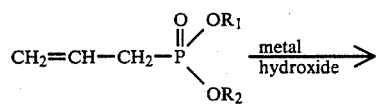

-continued

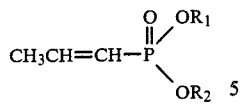

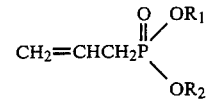

wherein R₁ and R₂ are as described above. The process of this invention can be conveniently carried out by contacting an appropriate allylic phosphonate diester compound with a catalytically effective amount of one or more metal hydroxide compounds, either neat or in an aprotic organic solvent which is non-reactive under the process conditions.

Metal hydroxides which can be used in the process of this invention can vary widely. Illustrative of useful metal hydroxides are alkaline earth metal hydroxides and alkali metal hydroxides. Preferred for use in the practice of this invention are alkali metal hydroxides, and particularly preferred for use are potassium and sodium hydroxide, which hydroxides are preferred primarily because of their low cost and ready availability.

The form of the metal hydroxide is not critical. For example, the metal hydroxide can be used in solid form or dissolved in an appropriate reaction solvent.

A "catalytically effective amount" of the metal hydroxide is used. As used herein, a "catalytically effective amount" is an amount of the metal hydroxide which is capable of catalyzing the isomerization of the allylic phosphonate diester into the corresponding vinylic phosphonate diester to any extent. Generally, the amount of metal hydroxide employ is at least about 1 mole percent based on the moles of allylic phosphonate diester employed. In the preferred embodiments of the invention the amount of the metal hydroxide employed will vary from about 1 to about 25 mole percent, and in the particularly preferred embodiments will vary from about 10 to about 20 mole percent on the aforementioned basis. Amongst these particularly preferred embodiments most preferred are those embodiments in which the mole percent of alkali metal hydroxide varies from about 12 to about 18 mole percent on the aforementioned basis.

As was noted above, the reaction can be carried out neat or in an appropriate solvent. The reaction is usually carried out neat when the allylic phosphonate diester reactant is liquid under the reaction conditions. The reaction solvent can be used when the phosphonate diester reactant is either a liquid or solid. In the preferred embodiments of the invention, the reaction is carried out in an appropriate reaction solvent. Useful organic solvents include those solvents which do not include any functional groups which are reactive with the reactants. Illustrative of such solvents are non-reactive alcohols such as methanol, ethanol, propanol and the like; halohydrocarbons such as carbon tetrachloride, methylene dichloride, chloroform, chlorotrifluoromethane, dichloridifluoroethane, trichlorotrifluoroethane, and the like; aromatic solvents such as benzene, toluene, xylene and the like. Preferred organic solvents for use in the practice of this invention are alkanols having from 1 to about 7 carbon atoms. Particularly preferred reaction solvents are methanol and ethanol.

Allylic phosphonate diester compounds which are useful as reactants in the conduct of the process of this invention are of the formula:

in which R₁ and R₂ are as described above.

Illustrative of permissible R₁ and R₂ groups are alkyl such as methyl, ethyl, isopropyl, pentyl, hexyl, isobutyl, heptyl and the like; cycloalkyl such as cyclobutyl, cyclopropyl, cyclohexyl, cyclopentyl and the like; aryl such as phenyl, naphthyl and the like; alkylaryl, such as 2,4-dimethylphenyl, 4-(tert-butyl)phenyl, 3-methylphenyl, and the like; and arylalkyl, such as 2-phenylethyl, 3-phenylbutyl, 4-phenylbutyl, 2-phenylisopropyl and the like.

As was noted above, R₁ and R₂ substituents may be substituted with one or more functional groups which are relatively non-reactive with the reactants, product and catalyst employed in the process under the process conditions. Illustrative of such non-reactive functional groups are halogen, i.e. fluorine, chlorine, bromine or iodine, alkoxy i.e., methoxy, ethoxy, propoxy and the like, as well as nitro, cyano, carboxy, alkoxycarbonyl, perfluoroalkyl, i.e., trifluoromethyl, and like non-reactive functional groups.

Preferred for use in the practice of this invention are allylic phosphonate ester compounds in which R₁ and R₂ are the same and are alkyl having from 1 to about 8 carbon atoms, and particularly preferred for use are compounds in which R₁ and R₂ are the same and are alkyl having from 1 to about 4 carbon atoms. Amongst these particularly preferred embodiments most preferred are those embodiments in which R₁ and R₂ are the same and are methyl or ethyl.

Allylic phosphonate ester compounds which can be used in the practice of this invention can be obtained from commercial sources or prepared in accordance with conventional procedures. For example, useful allylic phosphonate ester compounds can be conveniently prepared by reacting trialkylphosphite compounds with an excess of an alkyl or aryl halide as described in greater detail in Compt. Ren. 259:2244–7 (1964).

The temperature employed in the process of this invention is critical and can be varied widely depending on factors known to those of skill in the art. Reaction temperature will generally vary from about 0° C. to about 150° C. Temperatures within the range of from about 0° C. to about 100° C. are preferred, and reaction temperatures of from about 25° C. to about 80° C. are particularly preferred. In the most preferred of the invention, embodiments the reaction is conducted at room temperature.

Reaction pressures are also not critical and can be varied widely. The reaction can be carried out at superatmospheric, atmospheric and sub-atmospheric pressures. For convenience, the reaction is carried out at autogenous pressure.

The process of this invention is carried out over a period of time sufficient to produce and desired compound in adequate yield. Reaction times are influenced to a significant extent by the reaction temperature; the concentration and choice of metal hydroxide compound and allylic phosphonate ester reactants; the choice and concentration of reaction solvent and by other factors known to those skilled in the art. In general, reaction times can vary from about a few minutes to 24 hours or longer. In most instances, when employing preferred reaction conditions, reaction times will be found to vary from about 1 hour to about 3 hours.

The process of this invention can be conducted in a batch, semicontinuous or continuous fashion. The reaction can be conducted in a single reaction zone or in a plurality of reaction zones, in series or in parallel, or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing of the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactant and catalyst may be initially introduced into th reaction zone batchwise or they may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactant and catalyst.

The product vinylic phosphonate diester compound can be isolated from the reaction mixture and purified employing conventional techniques. Illustrative of such techniques are evaporation, distillation, solvent extraction and recrystallization.

The vinylic phosphonate diester compounds prepared in accordance with the process of this invention have many and varied uses. For example, such compounds can be used as precursors in the preparation of plant growth regulators as described in detail German Offen. No. 2,153,149, or as precursors in the preparation of phosphatase inhibitors as described in Bartlett, et al. Tet Letters 24:2937 (1983). Alternatively, compounds prepared in accordance with the process of this invention can be used as precursors in the preparation of flame retardants or shrinkage retardants as described in U.S. Pat. Nos. 4,129,710, 2,784,206 and 2,784,169; Gen. Offen. 2,745,982; J. Appl. Polym. Sci. 22:2403-14 (1978) and J. Org. Chem. (USSR) 19:1789 (1983).

The following examples are presented to more particularly illustrate the process of this invention, and are not to be construed as limitations thereto.

EXAMPLE I

O,O-Dimethylallylphosphonate 3 g ($2 \times 10^{-2}$ mol) and 0.3 g ($5.3 \times 10^{-3}$ mol) potassium hydroxide dissolved in 10 mL of methanol were refluxed for 15 min. The methanol was removed by vacuum distillation. The colorless oil which remained consisted of the following composition: 91.6% 1-methyl,2-vinyl-O,O-dimethyl phosphonate and 8.4% O,O-dimethylallylphosphonate. This material is adaquately pure for additional reactions or if substantially pure material is required may be subjected to fractional vacuum distillation (0.1 mm, 90°-100° C.).

NMR (d-CHCl$_3$, TMS): $\delta$6.8(m), 5.63(m), 3.73(s), 3.60(s), 1.93(m).

EXAMPLE II

O,O-Dimethylallyl phosphonate 3 g ($2 \times 10^{-2}$ mol) and 0.3 g ($5.3 \times 10^{-3}$ mol) of solid potassium hydroxide were stirred at room temperature. As the potassium hydroxide dissolved, the solution turned deep yellow. After 15 minutes, the 1-methyl,2-vinyl,O,O-dimethyl phosphonate was removed by vacuum distillation. The colorless composition: 93% O,O-dimethylvinylphosphonate; 7% 1-methyl,2-vinyl,O,O-dimethyl phosphonate.

EXAMPLE III

O,O-Dimethyl allylphosphonate 3 g ($2 \times 10^{-2}$ mol) and 0.3 g ($5.3 \times 10^{-3}$ mol) of solid potassium hydroxide were stirred at ambient temperature for 15 minutes. At this point, NMR analysis indicated that the reaction was >98% complete. The reaction was quenched with 20 mL of a saturated NH$_4$Cl solution and the product extracted with CH$_2$Cl$_2$. The CH$_2$Cl$_2$ was removed under reduced pressure to yield 2.9 g (97%) of a colorless oil, identified as 1-methyl,2-vinyl,O,O-dimethyl phosphonate.

NMR (d-CHCl$_3$, TMS): $\delta$6.8(m), 3.73(s), 3.60(s), 1.93(m).

EXAMPLE IV

O,O-Dimethylallylphosphonate 3 g ($2 \times 10^{-2}$ mol) and 0.3 g ($5.3 \times 10^{-3}$ mol) of solid potassium hydroxide were stirred at ambient temperature for 15 minutes. The reaction was quenched and the product isolated as described in EXAMPLE III. The colorless oil was subjection to vacuum distillation (0.1 mm, 90°-100° C.) to provide composition containing greater than 94% O,O-dimethylvinylphosphonate.

What is claimed is:

1. A process for the preparation of a vinylic phosphonate diester compound of the formula:

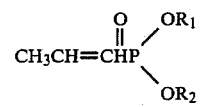

from a corresponding allyl phosphonate diester of the general formula:

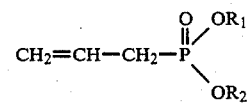

which comprises isomerizing said allyl phosphonate diester at a temperature of from about 0° C. to about 150° C. with a catalytically effective amount of one or more metal hydroxides, selected from the group consisting of alkali metal and alkaline earth metal hydroxides, wherein:

R$_1$ and R$_2$ are the same or different and are alkyl, cycloalkyl, arylalkyl or alkylaryl, either unsubstituted or substituted with one or more substituents which are inert under the process conditions.

2. A process according to claim 1 wherein $R_1$ and $R_2$ are the same.

3. A process according to claim 2 wherein $R_1$ and $R_2$ are unsubstituted.

4. A process according to claim 3 wherein $R_1$ and $R_2$ are alkyl having form 1 to about 8 carbon atoms.

5. A process according to claim 4 wherein $R_1$ and $R_2$ are alkyl having from 1 to about 4 carbon atoms.

6. A process according to claim 5 wherein $R_1$ and $R_2$ are methyl or ethyl.

7. A process according to claim 1 wherein said one or more metal hydroxides are selected from the group consisting of alkali metal hydroxides.

8. A process according to claim 7 wherein said one or more alkali metal hydroxides are selected from the group consisting of sodium hydroxide and potassium hydroxide.

9. A process according to claim 8 wherein said allyl phosphonate ester is isomerized with potassium hydroxide.

10. A process according to claim 1 wherein the amount of said metal hydroxide is at least about 1 mole percent based on the total moles of allyl phosphonate diester.

11. A process according to claim 10 wherein the amount of said metal hydroxide is from about 1 to about 25 mole percent.

12. A process according to claim 9 wherein the amount of said metal hydroxide is from about 10 to about 20 mole percent.

13. A process according to claim 1 wherein said isomerization temperature is from about 0° C. to about 100° C.

14. A process according to claim 1 wherein said allyl phosphonate compound is a liquid under the isomerization conditions and said isomerization is carried out neat.

15. A process according to claim 1 wherein said isomerization is carried out in a solvent which is nonreactive with the reactant and catalyst under the process conditions.

16. A process according to claim 15 wherein the solvent is selected from the group consisting of benzene, monoalkylated benzene, dialkylated benzene and alkanols.

17. Process according to claim 13 wherein said solvent is an alkanol having from 1 to about 6 carbon atoms.

18. A process according to claim 1 wherein the isomerization is conducted at ambient temperature.

19. A process according to claim 15 wherein the the isomerization is performed at the reflux temperature of the solvent.

20. A process according to claim 1 wherein the vinylphosphonate ester product is isolated by vacuum distillation.

21. A process according to claim 1 wherein said vinylic phosphonate diester product is isolated by solvent extraction.

22. A process according to claim 1 wherein solid one or more metal hydroxides are used.

23. A process according to claim 1 wherein the one or more metal hydroxide compounds are dissolved in a solvent which is non-reactive under the process conditions.

* * * * *